United States Patent [19]

Morrison

[11] Patent Number: 5,524,375
[45] Date of Patent: Jun. 11, 1996

[54] COMPOSITION AND METHOD FOR GATHERING EARTHWORMS

[75] Inventor: Fred J. Morrison, Naples, Fla.

[73] Assignee: Natural Chemicals, Inc., Naples, Fla.

[21] Appl. No.: 356,491

[22] Filed: Dec. 15, 1994

[51] Int. Cl.⁶ .................................................. A01M 23/00
[52] U.S. Cl. ............................................................. 43/1
[58] Field of Search ............................ 43/1, 4; 585/355, 585/356

[56] References Cited

U.S. PATENT DOCUMENTS

| | | | |
|---|---|---|---|
| 3,239,413 | 3/1966 | Chaney | 43/1 |
| 4,178,711 | 12/1979 | Mermal et al. | 43/1 |
| 4,570,372 | 3/1986 | Lukas | 43/1 |
| 4,616,036 | 10/1986 | Hodgin | 514/470 |
| 4,743,620 | 3/1988 | Hodgin | 514/515 |
| 4,934,087 | 6/1990 | Zanon et al. | 43/1 |
| 5,327,674 | 7/1994 | Powell | 43/71 |

*Primary Examiner*—Richard K. Seidel
*Assistant Examiner*—Randolph S. Herrich
*Attorney, Agent, or Firm*—Quarles & Brady

[57] ABSTRACT

A method for gathering worms, and particularly earthworms, includes the step of applying to the surface of soil containing the earthworms a composition containing a terpene. The terpene is preferably limonene, and most preferably d-limonene. The composition is preferably diluted in water. The earthworms come substantially to the surface of the soil within a few minutes, and can then be gathered by hand or another suitable technique. A composition for gathering worms is also disclosed.

11 Claims, No Drawings

COMPOSITION AND METHOD FOR GATHERING EARTHWORMS

FIELD OF THE INVENTION

This invention relates generally to a composition and method for gathering worms.

BACKGROUND OF THE INVENTION

Worms, and particularly earthworms, are frequently used as bait for freshwater fishing. Earthworms are found in soil in many places, however, gathering the earthworms can be a difficult task. The earthworms sometimes must be gathered from below the surface of the soil, and in hot weather the earthworms are sometimes found in deeper levels of the soil. Digging for the earthworms is a tiring and time consuming task. It would be desirable to provide a composition and method for gathering earthworms which would not require tedious digging in the soil.

Earthworms come to the surface of the soil at night when it is cool. It is both difficult and inconvenient to gather earthworms at night, and impossible if the fishing trip was not planned in advance. It would be desirable to be able to gather earthworms easily during the day.

The earthworms should remain alive to be the most effective fishing bait. It is therefore important that the earthworms remain viable. Also, any method or composition for gathering earthworms should not be harmful to the environment.

SUMMARY OF THE INVENTION

It is an object of the invention to provide a composition and method for gathering earthworms which is less tedious and time consuming than digging.

It is another object of the invention to provide a composition and method for gathering earthworms which will permit the gathering of earthworms during daylight hours.

It is still another object of the invention to provide a composition and method for gathering earthworms which is environmentally safe and does not kill the earthworms.

These and other objects are provided by a composition and method for gathering earthworms which comprises the application of limonene to the soil. The limonene is preferably d-limonene. This compound is found in citrus oil. Additional compounds, such as defoaming agents, can also be added.

The limonene is preferably diluted in water, which mixture is then applied to the surface of the soil. The earthworms come to the surface of the soil, usually in less than about five minutes. The earthworms can then be gathered and placed in a suitable container.

The dilution of the composition in the water is preferably between about 1/5 and 1/20 ounces per gallon of water, and is most preferably about 1/10 ounces per gallon of water.

DETAILED DESCRIPTION OF THE PREFERRED EMBODIMENTS

Compositions according to the invention preferably comprise limonene, or analogues and derivatives thereof, and most preferably comprise d-limonene. The d-limonene is preferably diluted in a suitable solvent, preferably water.

The dilution of the composition in water can vary. It is currently preferred that the concentration of the composition in water be between about 1/5 and about 1/20 ounces per gallon of water. It is most preferred that the concentration of the composition in the water be about 1/10 ounces per gallon of water.

It is possible that other compounds can be substituted for, or added to, the d-limonene in compositions according to the invention. Limonene occurs naturally in both d- and l-forms. Limonene is found in lemon, bergamot, caraway, orange, and other oils, as well as peppermint and spearmint oils. Limonene is a terpene of the general formula $C_{10}H_{16}$. This class of isomeric hydrocarbons also includes myrcene and pinene. The terpenes are found in many essential oils, including conifers. These compounds, and derivatives and analogues thereof, may also be suitable for use in the invention.

A most preferred composition according to the invention includes limonene, myrcene, pinene, and gamma terpinene. This composition has been found to have improved anti-foaming characteristics. This composition preferably comprises, by volume, about 0.3% to about 0.5% pinene, about 1.5% to about 1.9% myrcene, about 0.1% to about 0.6% gamma terpinene, and the balance d-limonene. The addition of known anti-foaming agents is also within the scope of the invention.

The composition can be applied directly to the surface of the soil after dilution in water. Preparation of the soil is generally not necessary. The preferred distribution of the diluted composition is about 0.08 gallons per square foot. More should be applied in very dry or very cold conditions, because the worms are deeper in the soil. The liquid will penetrate through the surface of the soil, and the worms will usually rise to the surface of the soil within about five minutes. The method is effective in the day or night. The worms can then be gathered by hand, or by other suitable techniques. The invention is useful for different types of worms, and particularly for earthworms.

This invention can be embodied in other forms without departing from the spirit and essential attributes thereof, and accordingly, reference should be had to the following claims, rather than to the foregoing specification, as indicating the scope of the invention.

I claim:

1. A method for gathering worms, comprising the steps of:
   applying to the surface of soil containing the worms a composition comprising limonene;
   waiting for the worms to come substantially to the surface of the soil; and,
   gathering the worms.

2. The method of claim 1, wherein the worms are earthworms.

3. The method of claim 1, wherein said composition comprises, by volume, between about 0.3% to about 0.5% pinene, about 15% to about 19% myrcene, about 0.1% to about 0.6% gamma terpinene, and the balance limonene.

4. The method of claim 1, wherein the limonene is d-limonene.

5. The method of claim 4, wherein said composition is diluted in water prior to application to the soil.

6. The method of claim 5, wherein the dilution of the composition is between about 1/5 and about 1/20 ounces per gallon of water.

7. The method of claim 6, wherein the dilution of the composition is about 1/10 ounces per gallon of water.

8. The method of claim 7, wherein about 0.08 gallons per square foot of said composition is distributed over the surface of said soil.

9. A method for gathering worms, comprising the steps of:

applying to the surface of soil containing the earthworms a composition comprising at least one terpene;

waiting for the earthworms to come substantially to the surface of the soil; and, gathering the worms.

10. The method of claim 9, wherein said terpene is at least one selected from the group consisting of limonene, myrcene and pinene, and mixtures thereof.

11. The method of claim 10, wherein said limonene is d-limonene.

* * * * *